US005712153A

United States Patent [19]
Damhus et al.

[11] Patent Number: 5,712,153
[45] Date of Patent: Jan. 27, 1998

[54] DYE TRANSFER INHIBITION

[75] Inventors: Ture Damhus; Ole Kirk, both of Copenhagen; Gitte Pedersen, Frederiksberg C, all of Denmark; Manuel Garcia Venegas, Cincinnati, Ohio; Bjørn Eggert Christensen, Holte; Palle Schneider, Ballerup, both of Denmark

[73] Assignee: Novo Nordisk A/S, Bagsvaerd, Denmark

[21] Appl. No.: 448,209

[22] Filed: May 23, 1995

Related U.S. Application Data

[62] Division of Ser. No. 105,222, Aug. 11, 1993, Pat. No. 5,605,832, which is a division of Ser. No. 599,331, Oct. 17, 1990, Pat. No. 5,273,896, which is a continuation-in-part of Ser. No. 421,414, Oct. 13, 1989, abandoned.

[51] Int. Cl.⁶ .............................. C12N 9/08; C07K 7/00; D06M 16/00
[52] U.S. Cl. .......................... 435/263; 435/192; 435/264
[58] Field of Search ....................... 435/263, 264, 435/192

[56] References Cited

U.S. PATENT DOCUMENTS 5,273,896 12/1993 Pedersen .......................... 435/263

FOREIGN PATENT DOCUMENTS

| 0173378 | 5/1986 | European Pat. Off. |
| 282588 | 12/1927 | Switzerland . |
| 2101167 | 1/1983 | United Kingdom . |

*Primary Examiner*—Carolyn Paden
*Attorney, Agent, or Firm*—Steve T. Zelson, Esq.; Valeta Gregg, Esq.

[57] ABSTRACT

The transfer of a textile dye from a dyed fabric to another fabric during washing or rinsing is inhibited by adding an enzyme exhibiting peroxidase activity or an enzyme exhibiting a suitable oxidase activity to the wash liquor in which said fabrics are washed and/or rinsed. Peroxidase is produced extracellularly by some strains of *Bacillus pumilus*. The novel peroxidase preparation from *B. pumilus* is a microperoxidase, i.e. it contains hemopeptide as an active component. The preparation has improved stability at high temperature, at high pH and at high concentrations of hydrogen peroxide. It can be produced without undesired catalase activity.

1 Claim, 11 Drawing Sheets

DYE TRANSFER INHIBITION

CROSS-REFERENCE TO RELATED APPLICATION

This is a divisional application of application Ser. No. 08/105,222, filed Aug. 11, 1993, now U.S. Pat. No. 5,605,832 which is a divisional of Ser. No. 07/599,331 filed Oct. 17, 1990 now U.S. Pat. No. 5,273,896, which is a continuation-in-part of Ser. No. 07/421,414 filed Oct. 13, 1989 now abandoned. The contents of Ser. No. 08/105,222 are incorporated herein by reference in their entirety.

FIELD OF INVENTION

The present invention relates to an enzymatic process for inhibiting the transfer of dye from a dyed fabric to another fabric during washing, to a bleaching agent for use in the process, and to a process for bleaching dyes in solution. This invention also relates to a hemopeptide with peroxidase activity, to a peroxidase preparation, and to production and use of such a preparation.

BACKGROUND OF THE INVENTION

The use of bleaching agents in washing procedures and as constituents of detergent compositions is well known in the art. Thus, bleaching agents are incorporated in or sold as constituents of a major part of the commercially available detergent compositions. Important conventional bleaching agents incorporated in detergent compositions are compounds which act as precursors of hydrogen peroxide formed in the course of the washing procedure. Perborates and percarbonates are the most important examples of compounds which are employed as bleaching agents and which exert a bleaching effect in this fashion. The detailed mechanism of bleaching by means of these bleaching agents is not known at present, but it is generally assumed that the hydrogen peroxide formed during washing converts coloured substances (responsible for stains on fabric) into noncoloured materials by oxidation and that some oxidation of the coloured substances may also take place due to their direct interaction with perborate or percarbonate.

One drawback of these commonly used bleaching agents is that they are not particularly efficient at the lower temperatures at which coloured fabrics are usually washed. Their efficiency may be enhanced by the use of activators (e.g. organic acid anhydrides, esters or imides) which give rise to the formation of peracids.

Apart from being employed for bleaching stains on fabric, such conventional bleaching agents have also been suggested for preventing surplus dyes from coloured fabrics which leach from the fabrics when these are washed from being deposited on other fabrics present in the same wash (this phenomenon is commonly known as dye transfer). The problem of dye transfer, of course, is most noticeable when white or light-coloured fabrics are washed together with fabrics of a darker colour from which dye is leached during washing.

It has, however, been found that the currently employed bleaching agents, whether activated or not, are not particularly effective in inhibiting dye transfer, possibly because the rate at which they oxidize dissolved dyes is rather slow. On the other hand, peracids formed from the bleaching activators are active against dyes on fabric so as to cause discolouration of the fabric in question.

U.S. Pat. No. 4,077,768 discloses the use of iron porphin, haemin chloride or iron phthalocyanine, or derivatives thereof together with hydrogen peroxide for dye transfer inhibition. It is indicated that these compounds act as catalysts for the bleaching process whereby they provide an increase in the rate at which dissolved dyes are oxidised (or, in other words, bleached) without causing any discolouration of the dye in the fabric. However, these catalysts are destroyed by the presence of excess hydrogen peroxide which makes it necessary to control the release of hydrogen peroxide so that only the quantity of hydrogen peroxide needed to effect the inhibition of dye transfer should be present in the wash water at any time. Such controlled release of the bleaching agent may be difficult to achieve.

Peroxidase activity catalyses oxidation of a substrate (an electron or hydrogen donor such as lignin) with hydrogen peroxide.

High-molecular peroxidases (E.C. 1.11.1.7) are produced intracellularly by some microorganisms. Thus, S. Loprasert et al., *Journal of General Microbiology* (1983), 134, 1971–1976 describe a peroxidase-catalase from *Bacillus stearothermophilus* with molecular weight 175,000 and U.S. Pat. No. 4,698,306 describes a peroxidase from Coprinus with molecular weight 37,000–41,000. Also, so-called microperoxidases of mammalian origin are known; these are hemopeptides, typically with molecular weight in the range 1,500–3,000, exhibiting peroxidase activity (e.g. DE 3134526).

Use of peroxidase together with hydrogen peroxide or a hydrogen peroxide precursor has been suggested e.g. in bleaching of pulp for paper production (SE 88/0673), in treatment of waste water from pulp production (U.S. Pat. No. 4,623,465, JP-A 2-31887) and for improved bleaching in laundry detergents (WO 89/09813). Pending U.S. patent application Ser. No. 07/421,414 (filed Oct. 13, 1989) and a co-pending PCT application disclose the use for dye transfer inhibition during laundering.

It is the object of the invention to provide an improved peroxidase for these purposes. The peroxidase should be active and stable at high temperature and $H_2O_2$ concentration, especially at alkaline conditions. It should be free of catalase as this activity breaks down hydrogen peroxide that is needed in the reaction. For better production economy, the peroxidase should be microbial and should be produced extracellularly by the microorganism in question.

SUMMARY OF THE INVENTION

It has surprisingly been found possible to bleach coloured substances leached from dyed textiles or from textiles soiled with a colourant in a solution of wash liquor thereby preventing the coloured substance in question from being deposited on other textiles in the wash liquor, when enzymes utilizing hydrogen peroxide or molecular oxygen for the oxidation of organic or inorganic substances, including coloured substances, are added to the wash liquor. Such enzymes are usually termed peroxidases and oxidases, respectively.

Accordingly, the present invention relates to a process for inhibiting the transfer of a textile dye from a dyed fabric to another fabric when said fabrics are washed and/or rinsed together in a wash liquor, the process comprising adding an enzyme exhibiting peroxidase activity or an enzyme exhibiting a suitable oxidase activity to the wash liquor in which said fabrics are washed and/or rinsed. In the present context, the term "enzyme exhibiting peroxidase activity" is understood to indicate an enzyme with a mode of action similar to that of a peroxidase and will be used synonymously therewith. Similarly, the term "enzyme exhibiting a suitable oxidase activity" is understood to indicate an enzyme with a similar mode of action to that of an oxidase and is meant to be synonymous therewith in the following. Suitable oxidases include those which act on aromatic compounds such as phenols and related substances.

One or more substrates for the enzyme may also be added at the beginning of or during the washing and/or rinsing process, in particular when the enzyme is one with peroxidase activity as, in the case of oxidases, molecular oxygen is usually present in sufficient quantities. When the enzyme used in the process of the invention is a peroxidase, hydrogen peroxide or a precursor of hydrogen peroxide, preferably perborate or percarbonate, will therefore typically be added as the substrate.

It is well recognized in the art (cf. for instance B. C. Saunders et al., *Peroxidase*, London, 1964, p. 10 ff.) that peroxidases act on various amino and phenolic compounds resulting in the production of a colour. In view of this, it must be considered surprising that peroxidases (and certain oxidases) may also exert an effect on coloured substances in solution such that dye transfer is inhibited. While the mechanism governing the ability of these enzymes to effect dye transfer inhibition has not yet been elucidated, it is currently believed that the enzymes act by reducing hydrogen peroxide or molecular oxygen and oxidizing the coloured substance (donor substrate) dissolved or dispersed in the wash liquor, thereby either generating a colourless substance or providing a substance which is not adsorbed to the fabric. This reaction is shown in Reaction Scheme 1 below (for peroxidases) and Reaction Scheme 2 below (for oxidases useful for the present purpose).

Reaction Scheme 1:
Donor substrate+$H_2O_2$→oxidized donor+2 $H_2O$
Reaction Scheme 2:
Donor substrate+$O_2$→oxidized donor+2 $H_2O$ It has previously been reported that peroxidases may decolourize certain pigments (cf. for instance W. Schreiber, *Biochem. Biphys. Res. Commun.* 63 (2), 1975, pp. 509–514, describing the degradation of 3-hydroxyflavone by horseradish peroxidase; A. Ben Aziz, *Phytochemistry* 10, 1971, pp. 1445–1452, describing the bleaching of carotene by means of a peroxidase; and B. P. Wasserman, *J. Food Sci.* 49, 1984, pp. 53614 538, describing the decolourization of betalain by horseradish peroxidase). Ben Aziz et al. and Wasserman et al. present the bleaching action of peroxidases on carotene and betalain, respectively, as a problem when using these pigments as food colourants, which problem must be counteracted by including an anti-oxidant in the foodstuff in question. Thus, they do not consider the peroxidase-mediated bleaching of these pigments to have any practical utility in itself.

Although these publications describe test methods whereby the respective pigments are incubated with the enzyme in solution, the pigments in question are all pure compounds of natural origin and are also readily bleached by the bleaching agents usually incorporated in modern detergents (cf. for instance *Second World Conference on Detergents*, A. R. Baldwin (ed.), American Oil Chemist's Society, 1978, pp. 177–180).

Contrary to this, the commonly used textile dyes, when dissolved or dispersed in wash liquors, are generally resistant to oxidation by atmospheric oxygen and also, to a greater or lesser extent, to the bleaching agents currently used in detergents which, as noted in U.S. Pat. No. 4,077,768, are inefficient dye transfer inhibitors as they act too slowly on the dispersed or dissolved dyes. Under these circumstances, it must be considered surprising that the enzymes used in the present process are, in fact, able to oxidize these dyes. Other commonly used bleaching agents which may have an effect on textile dyes in solution or dispersion, e.g. hypochlorite, also attack dye on or in the fabrics, resulting in discolouration thereof. It is an important advantage of the enzymes used in the process of the invention that they do not cause any appreciable colour degradation in the dyed fabric itself. A comprehensive catalogue of commonly used textile dyes, both synthetic (such as azo dyes) and natural or nature-identical (by which is meant a substance which is produced synthetically, but which in structure and properties is identical to the natural compound), e.g. indigo, is found in the *Color Index*, 3rd ed. Vol. 1–8.

In another aspect, the present invention relates to a process for bleaching textile dyes in solution or dispersion, the process comprising adding an enzyme exhibiting peroxidase activity or an enzyme exhibiting a suitable oxidase activity to said solution or dispersion. It is contemplated that, apart from having utility in inhibiting dye transfer during a washing or rinsing process, the ability of these enzymes to bleach dyes in solution may also make them useful for treating waste water from the textile industry forming part of a waste disposal process.

In a further aspect, the present invention relates to a bleaching agent for inhibiting the transfer of a textile dye from a dyed fabric to another fabric when said fabrics are washed and/or rinsed together, the agent comprising an enzyme exhibiting peroxidase activity or an enzyme exhibiting a suitable oxidase activity. Apart from this utility, the bleaching agent may also be employed in the treatment of waste water from the textile and possibly also other industries, as indicated above.

We have also, surprisingly, discovered that peroxidase is produced extracellularly by some strains of *Bacillus pumilus*. The novel peroxidase preparation from *B. pumilus* is a microperoxidase preparation, i.e. it contains hemopeptide as an active component. The preparation has improved stability at high temperature, at high pH and at high concentrations of hydrogen peroxide. It can be produced without undesired catalase activity.

Accordingly, the invention provides a hemopeptide characterized by the amino acid sequence SEQ ID NO:3 having R linked to cysteine in position 1 and R' linked to histidine in position 5, wherein the sulphur atoms of the two cysteines in positions 1 and 4 are linked to the vinyl groups of heme, and R and R' each represents a peptide chain of 0–10 amino acids.

The invention also provides a peroxidase preparation, characterized by comprising as an active component a hemopeptide as defined above or one that contains a heme group linked to a peptide chain containing the amino acid sequence SEQ ID NO:4, wherein each Xaa represents any amino acid. In another embodiment the invention provides a peroxidase preparation, characterized by comprising one or more active components derived from *B. pumilus* with molecular weight in the range 800–2500, said preparation being further characterized by a pH optimum in the range 7.5–9, by retaining at least 50% residual activity after 2 hours at 80° C., and by having optimum activity at $H_2O_2$ concentration above 20 mM.

The invention further provides a method of producing a peroxidase preparation, characterized by comprising cultivation of a peroxidase-producing strain of *B. pumilus* followed by recovery of peroxidase.

Finally, the invention provides use of the above peroxidase preparation together with hydrogen peroxide (optionally formed in situ) in bleaching of lignin-containing material.

DETAILED DESCRIPTION OF THE INVENTION

Examples of suitable oxidases which act on aromatic compounds, in particular phenolic, e.g. polyphenolic, are catechol oxidase (EC 1.10.3.1) or laccase (EC 1.10.3.2). For the sake of convenience, such oxidases, and peroxidases are collectively termed bleaching enzymes in the following.

Bleaching enzymes which may be employed for the present purpose may be isolated from and are producible by plants (e.g. horseradish peroxidase) or microorganisms such as fungi or bacteria. Some preferred fungi include strains belonging to the subdivision Deuteromycotina, class Hyphomycetes, e.g. *Fusarium, Humicola, Tricoderma, Myrothecium, Verticillum, Arthromyces, Caldariomyces, Ulocladium, Embellisia, Cladosporium* or *Dreschlera,* in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartatum, Embellisia alli* or *Dreschlera halodes.*

Other preferred fungi include strains belonging to the subdivision Basidiomycotina, class Basidiomycetes, e.g. *Coprinus, Phanerochaete, Coriolus* or *Trametes,* in particular *Corpinus cinereus* f. *microsporus* (IFO 8371), *Coprinus macrorhizus, Pahnerochaete chyrsosporium* (e.g. NA-12) or *Coriolus versicolor* (e.g. PR 4 28-A).

Further preferred fungi include strains belonging to the subdivision Zygomycotina, class Mycoraceae, e.g. *Rhizopus* or *Mucor,* in particular *Mucor hiemalls.*

Some preferred bacteria include strains of the order Actinomycetales, e.g. *Streptomyces spheroides* (ATTC 23965), *Streptomyces thermoviolaceus* (IFO 12382) or *Streptoverticilum verticillium* ssp. verticillium.

Other preferred bacteria include *Bacillus pumillus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Other potential sources of useful bleaching enzymes (in particular peroxidases) are listed in B. C. Saunders et al., op. cit., pp. 41–43.

Methods of producing enzymes to be used according to the invention are described in the art, cf. for example *FEBS Letters* 1625, 173(1), *Applied and Environmental Microbiology,* Feb. 1985, pp. 273–278, *Applied Microbiol. Biotechnol.* 26, 1987, pp. 158–163, *Biotechnology Letters* 9(5), 1987, pp. 357–360, *Nature* 326, Ar. 2, 1987 *FEBS Letters* 4270, 209(2), p. 321, EP 179 486, EP 200 565, GB 2 167 421, EP 171 074, and *Agric. Biol. Chem.* 50(1), 1986, p. 247.

Particularly preferred bleaching enzymes are those which are active at the typical pH of washing liquors, i.e. at a pH of 6.5–10.5, preferably 6.5–9.5, and most preferably 7.5–9.5. Such enzymes may be isolated by screening for the relevant enzyme production by alkalophilic microorganisms, e.g. using the ABTS assay described in R. E. Childs and W. G. Bardsley, *Biochem. J.* 145, 1975, pp. 93–103.

Other preferred bleaching enzymes are those which exhibit a good thermostability as well as a good stability towards commonly used detergent components such as non-ionic, cationic, or anionic surfactants, detergent builders, phosphate etc.

Another group of useful bleaching enzymes are haloperoxidases, such as chloro- and bromoperoxidases.

The bleaching enzyme may furthermore be one which is producible by a method comprising cultivating a host cell transformed with a recombinant DNA vector which carries a DNA sequence encoding said enzyme as well as DNA sequences encoding functions permitting the expression of the DNA sequence encoding the enzyme, in a culture medium under conditions permitting the expression of the enzyme and recovering the enzyme from the culture.

A DNA fragment encoding the enzyme may, for instance, be isolated by establishing a cDNA or genomic library of a microorganism producing the enzyme of interest, such as one of the organisms mentioned above, and screening for positive clones by conventional procedures such as by hybridization to oligonucleotide probes synthesized on the basis of the full or partial amino acid sequence of the enzyme, or by selecting for clones expressing the appropriate enzyme activity, or by selecting for clones producing a protein which is reactive with an antibody against the native enzyme.

Once selected, the DNA sequence may be inserted into a suitable replicable expression vector comprising appropriate promotor, operator and terminator sequences permitting the enzyme to be expressed in a particular host organism, as well as an origin of replication enabling the vector to replicate in the host organism in question.

The resulting expression vector may then be transformed into a suitable host cell, such as a fungal cell, preferred examples of which are a species of *Aspergillus,* most preferably *Aspergillus oryzae* or *Aspergillus niger.* Fungal cells may be transformed by a process involving protoplast formation and transformation of the protoplasts followed by regeneration of the cell wall in a manner known per se. The use of *Aspergillus* as a host microorganism is described in EP 238,023 (of Novo Industri A/S), the contents of which are hereby incorporated by reference.

Alternatively, the host organisms may be a bacterium, in particular strains of Streptomyces and Bacillus, or *E. coli.* The transformation of bacterial cells may be performed according to conventional methods, e.g. as described in T. Maniatis et al., *Molecular Cloning: A Laboratory Manual,* Cold Spring Harbor, 1982.

The screening of appropriate DNA sequences and construction of vectors may also be carried out by standard procedures, cf. T. Maniatis et al., op. cit.

The medium used to cultivate the transformed host cells may be any conventional medium suitable for growing the host cells in question. The expressed enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

When the bleaching enzyme employed in the invention is a peroxidase, $H_2O_2$ may be added at the beginning or during the process, e.g. in an amount of 0.001–5 mM, particularly 0.01–1 mM. When using Corpinus peroxidase 0.01–0.25 $H_2O_2$ mM is preferred, and with *B. pumilus* peroxidase 0.1–1 mM $H_2O_2$. When the bleaching enzyme employed in the process of the invention is a peroxidase, it may be desirable to utilize an enzymatic process for hydrogen peroxide formation. Thus, the process according to the invention may additionally comprise adding an enzymatic system (i.e. an enzyme and a substrate therefor) which is capable of generating hydrogen peroxide at the beginning or during the washing and/or rinsing process.

One such category of hydrogen peroxide generating systems comprises enzymes which are able to convert molecular oxygen and an organic or inorganic substrate into hydrogen peroxide and the oxidized substrate, respectively. These enzymes produce only low levels of hydrogen peroxide, but they may be employed to great advantage in the process of the invention as the presence of peroxidase ensures an efficient utilization of the hydrogen peroxide produced.

Preferred hydrogen peroxide-generating enzymes are those which act on cheap and readily available substrates which may conveniently be included into detergent compositions. An example of such a substrate is glucose which may be utilized for hydrogen peroxide production by means of glucose oxidase. Other suitable oxidases are urate oxidase, galactose oxidase, alcohol oxidases, amine oxidases, amino acid oxidase and cholesterol oxidase.

It has surprisingly been found that the addition of another oxidisable substrate (for the bleaching enzyme used in the process of the invention) at the beginning or during the washing and/or rinsing process may enhance the dye transfer inhibitory effect of the bleaching enzyme employed. This is thought to be ascribable to the formation of short-lived radicals or other oxidised states of this substrate which participate in the bleaching or other modification of the coloured substance. Examples of such oxidisable substrates are metal ions, e.g. $Mn^{++}$, halide ions, e.g. chloride or bromide ions, or organic compounds such as phenols, e.g. p-hydroxycinnamic acid or 2,4-dichlorophenol. Other examples of phenolic compounds which may be used for the present purpose are those given in M. Kato and S. Shimizu, *Plant Cell Physiol.* 26(7), 1985, pp. 1291–1301 (cf. Table 1 in particular) or B. C. Saunders et al., opt. cit., p. 141 ff. The amount of oxidisable substrate to be added is suitably between about 1 µM and 1 mM.

In the process of the invention, the bleaching enzyme Will typically be added as a component of a detergent composition. As such, it may be included in the detergent composition in the form of a non-dusting granulate, a liquid, in particular a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216. The detergent composition may also comprise one or more substrates for the enzyme.

The detergent composition will additionally comprise surfactants which may be of the anionic, non-ionic, cationic, amphoteric, or zwitterionic type as well as mixtures of these surfactant classes. Typical examples of anionic surfactants are linear alkyl benzene sulfonates (LAS), alpha olefin sulfonates (AOS), alcohol ethoxy sulfates (AES) and alkali metal salts of natural fatty acids.

The detergent composition may further contain other detergent ingredients known in the art as e.g. builders, anti-corrosion agents, sequestering agents, anti-soil redeposition agents, perfumes, enzyme stabilizers, etc.

It is at present contemplated that, in the process of the invention, the bleaching enzyme may be added in an amount of 0.01–100 mg enzyme per liter of wash liquor.

The detergent composition may be formulated in any convenient form, e.g. as a powder or liquid. The enzyme may be stabilized in a liquid detergent by inclusion of enzyme stabilizers as indicated above. Liquid detergents may further include stabilized hydrogen peroxide precursors. Usually, the pH of a solution of the detergent composition of the invention will be 7–12 and in some instances 7.0–10.5. Other detergent enzymes such as proteases, lipases or amylases may be included in the detergent composition.

Hemopeptide

As noted above, one embodiment of the invention provides a microperoxidase, i.e. a hemopeptide characterized by the amino acid sequence SEQ ID NO:3 having R linked to cysteine in position 1 and R' linked to histidine in position 5, wherein the sulphur atoms of the two cysteines are linked to the two vinyl groups of heme, and R and R' each represents a peptide chain of 0–10 amino acids. These compounds can be prepared synthetically by methods known in the art, viz. by first synthesizing the peptide chain including the two cysteines and then letting this peptide react with heme, or they can be produced genetically by methods known in the art: a degenerate oligonucleotide probe is synthesized (based on the known amino acid sequence) and used to isolate the *B. pumilus* gene which encodes the precursor peptide chain of the microperoxidase. Modified microperoxidases are hereafter obtained by site directed mutagenesis (ref. Molecular Cloning, A Laboratory Manual, Cold Spring Harbor, 1989, Ed., J. Sambrook, E. F. Fritsh and T. Maniatis, ISBN 0-87969-309-6).

Preferred embodiments include a hemopeptide characterized by the amino acid sequence SEQ ID NO:5 having R' linked to histidine in position 9, a hemopeptide characterized by the amino acid sequence SEQ ID NO:6 having R linked to cysteine in position 1 and a hemopeptide characterized by the amino acid sequence SEQ ID NO:1; either of these may be shortened by one or more amino acids. These hemopeptides can be prepared by cultivation of a *B. pumilus* strain as described below.

A comparison of the sequences of hemopeptides of the invention with a known microperoxidase (DE 3134526) prepared by hydrolysis of cytochrome C from animal or plant shows that the novel microbial microperoxidase has very little homology with the known microperoxidase.

The prior art includes the hemopeptide having the amino acid sequence SEQ ID NO:2 wherein the sulphur atoms of the two cysteines at positions 5 and 8 are linked to the vinyl groups of heme.

A preferred embodiment of the present invention is the hemopeptide having the amino acid sequence SEQ ID NO:1 wherein the sulphur atoms of the two cysteines at positions 5 and 8 are linked to the vinyl groups of heme.

Cultivation of *B. pumilus*

*B. pumilus* strains that can be used in the practice of the invention are atypical in their ability to produce peroxidase. Some *B. pumilus* strains, including the type strain, have been found not to produce peroxidase.

Two peroxidase-producing strains are freely available with deposit numbers ATCC 12905 and NCIB 8600, and one strain (internal designation S 197) has been deposited by the applicant under the terms of the Budapest Treaty; the deposit date was 23 Jul. 1990, and the deposit number is DSM 6124.

ATCC indicates the American Type Culture Collection, 12301 Parklawn Drive, Rockville, Md. 20852, U.S.A., NCIB indicates the National Collection of Industrial and Marine Bacteria Ltd., Torry Research Station, P.O. Box 31, 135 Abbey Road, Aberdeen AB9 8DG, Scotland, and DSM indicates Deutsche Sammlung yon Mikroorganismen, Mascheroder Weg 1B, 3300 Braunschweig, West Germany.

Peroxidase-producing *B. pumilus* strains can be cultivated under aerobic conditions in a nutrient medium containing assimilable carbon and nitrogen together with other essential nutrient. The medium can be composed in accordance with principles known in the art.

During cultivation, the cells secrete peroxidase extracellularly, while they apparently produce catalase intracellularly. Extracellular production of the peroxidase is advantageous as it allows for high fermentation yield and simple recovery. Catalase is undesired for most applications of peroxidase, so the recovery of peroxidase preferably includes separation of cell mass from the cell broth while avoiding cell lysis, e.g. by filtration or centrifugation.

The resulting cell-free culture broth contains a mixture of hemopeptides with peroxidase activity, mainly with molecular weight in the range 800–2500. This can be used as such, optionally after concentration e.g. by evaporation or ultrafiltration. If desired, the various hemopeptides can be separated and purified to the desired degree by conventional methods, e.g. by column chromatography.

pH and temperature dependence

A crude peroxidase preparation of the invention (FIG. 1) and a similar purified preparation (FIG. 2) have slightly different pH optimum, but both are in the range 7–9.

The thermostability of peroxidase preparations of the invention (FIG. 3 and 4) is significantly better than a prior art microbial peroxidase (FIG. 5). A crude preparation according to the invention (FIG. 3) is more thermostable than a similar purified preparation. Both preparations of the invention retain more than 40% residual activity after 30 minutes incubation at 80° C. at pH 7.

Hydrogen peroxidase dependence

A peroxidase preparation of the invention (FIG. 6) shows increasing reaction rate up to 20 mM $H_2O_2$ (the highest tested). For comparison, a prior art microbial peroxidase shows decreasing reaction rate at $H_2O_2$ concentrations above 0.1 mM (FIG. 7).

Bleaching of lignin-containing material

Due to its good stability at high temperature and high $H_2O_2$ concentration, the peroxidase preparation of the invention is well suited for bleaching of lignin-containing materials, such as pulp for paper production or waste water from pulp manufacturing, together with hydrogen peroxide, e.g. as described in Ser. No. 88/0673, U.S. Pat. No. 4,623, 465 or JP-A 2-31887. Typical conditions are pH 7–10, 25°–70° C., 10–300 mM $H_2O_2$ and a dosage of 10–100 NOPA/g dry matter. Hydrogen peroxide may be added as such or formed in situ, e.g. by incorporation of a precursor, such as a perborate or percarbonate, or of an enzymatic system capable of generating hydrogen peroxide, e.g. an oxidase and a substrate therefor (such as glucose and glucose oxidase).

Other uses of peroxidase

Use of the peroxidase preparation of the invention is particularly advantageous at high temperature and/or high $H_2O_2$ concentration and at alkaline pH. As an example, it can be incorporated into a laundry detergent together with a hydrogen peroxide precursor (such as sodium perborate or percarbonate) to improve the bleaching of stains according to WO 89/09813.

As another example, the peroxidase preparation can be used to inhibit the transfer of a textile dye from a dyed fabric to another fabric when the fabrics are washed and/or rinsed together in a wash liquor, by adding it together with a hydrogen peroxide precursor to the wash liquor in which the fabrics are washed and/or rinsed.

Peroxidase assay (NOPA)

Peroxidase activity is measured at 2 mM $H_2O_2$. The following are mixed in a 30° C. thermostated 1 ml quartz cuvette:

200 μl 1 mM 4-aminoantipyrine (4-AA, Sigma No. A-4382, 0.2 mg/ml)

200 μl N-ethyl-N-sulphobutyl-m-toluidine-Na (ESBT, 5.86 mg/ml)

200 μl 0.5 M phosphate buffer, pH 7.0

200 μl enzyme sample, diluted to 0.02–0.10 NOPA/ml

200 μl 10 mM hydrogen peroxide is added, and the absorbance at 550 nm is followed for 1 minute. The activity is expressed in units denoted NOPA, calculated as the increase in absorbance within the first minute after addition of $H_2O_2$ multiplied by the dilution. The enzyme sample should be diluted so that the increase in absorbance per minute is within the limits 0.02 to 0.10.

BRIEF DESCRIPTION OF DRAWINGS

FIGS. 1 and 3 were made using cell-free culture broth prepared as in Example 13. FIGS. 2, 4, and 6 were made using pool III from Example 14.

EXAMPLES

Figure 1:
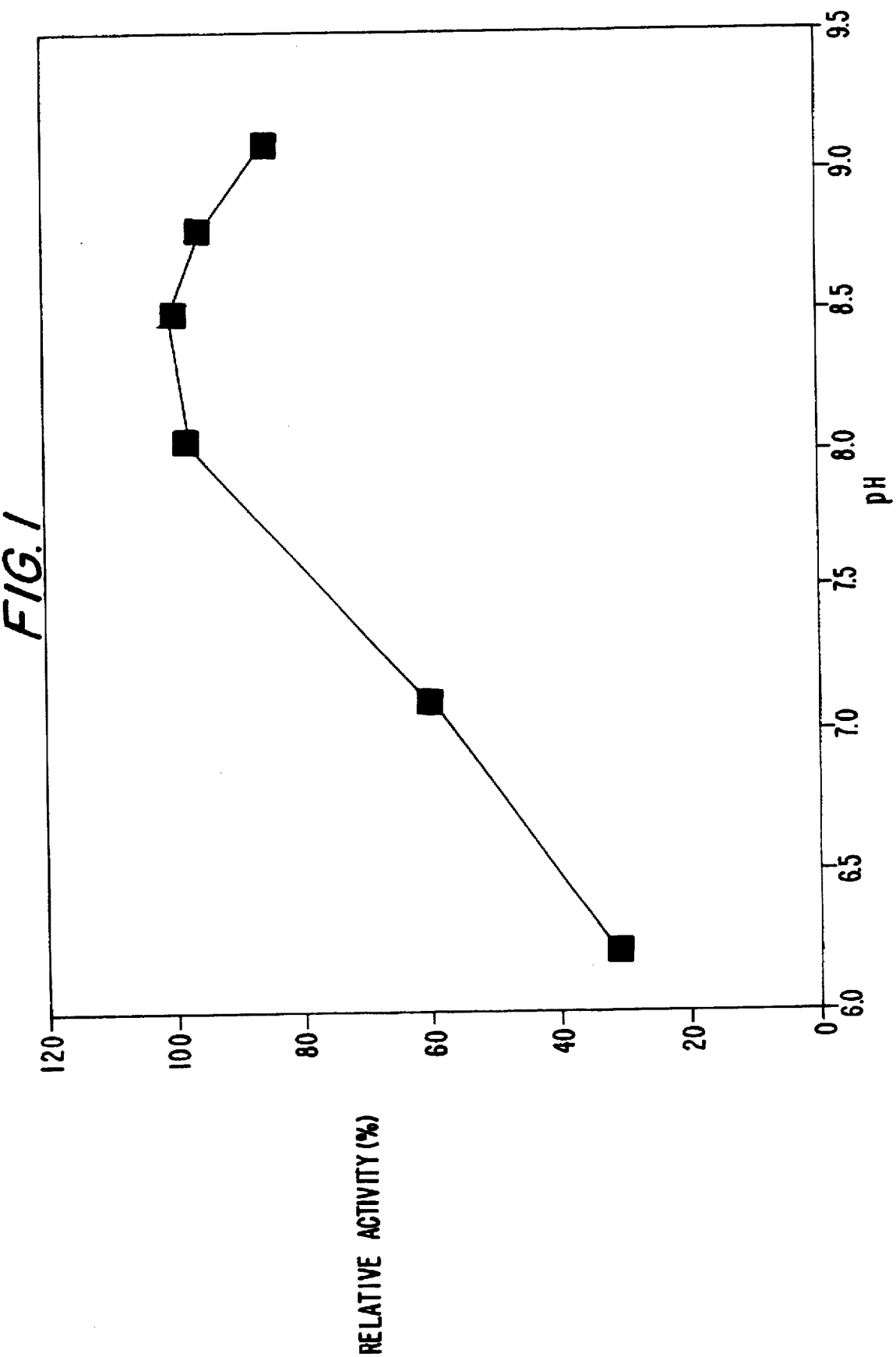
FIGS. 1 and 2 show the pH-activity curve of a crude and a purified peroxidase preparation, respectively, according to the invention, measured by the NOPA method, but varying the pH as shown.
Figure 2:
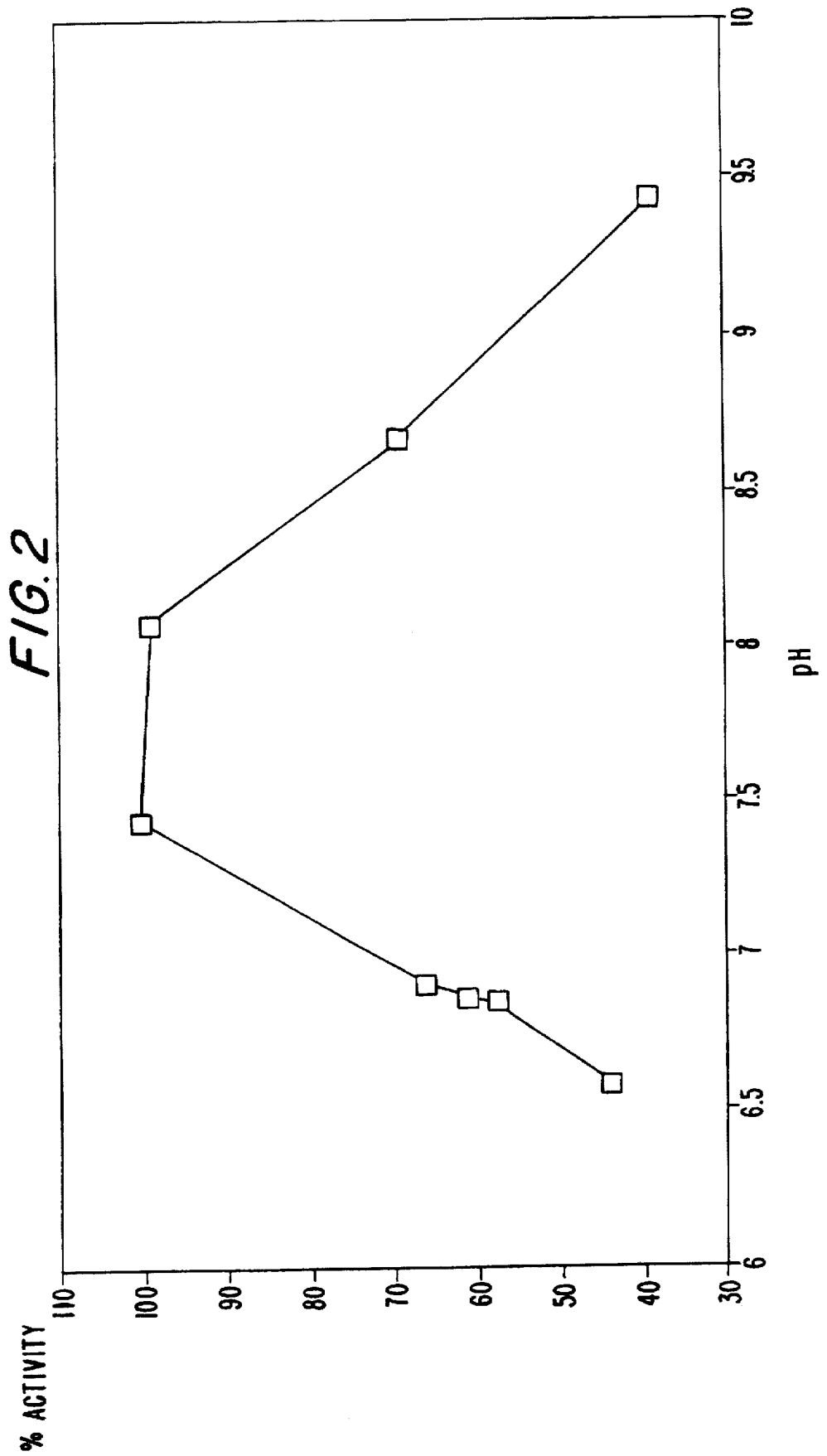
Figure 3:
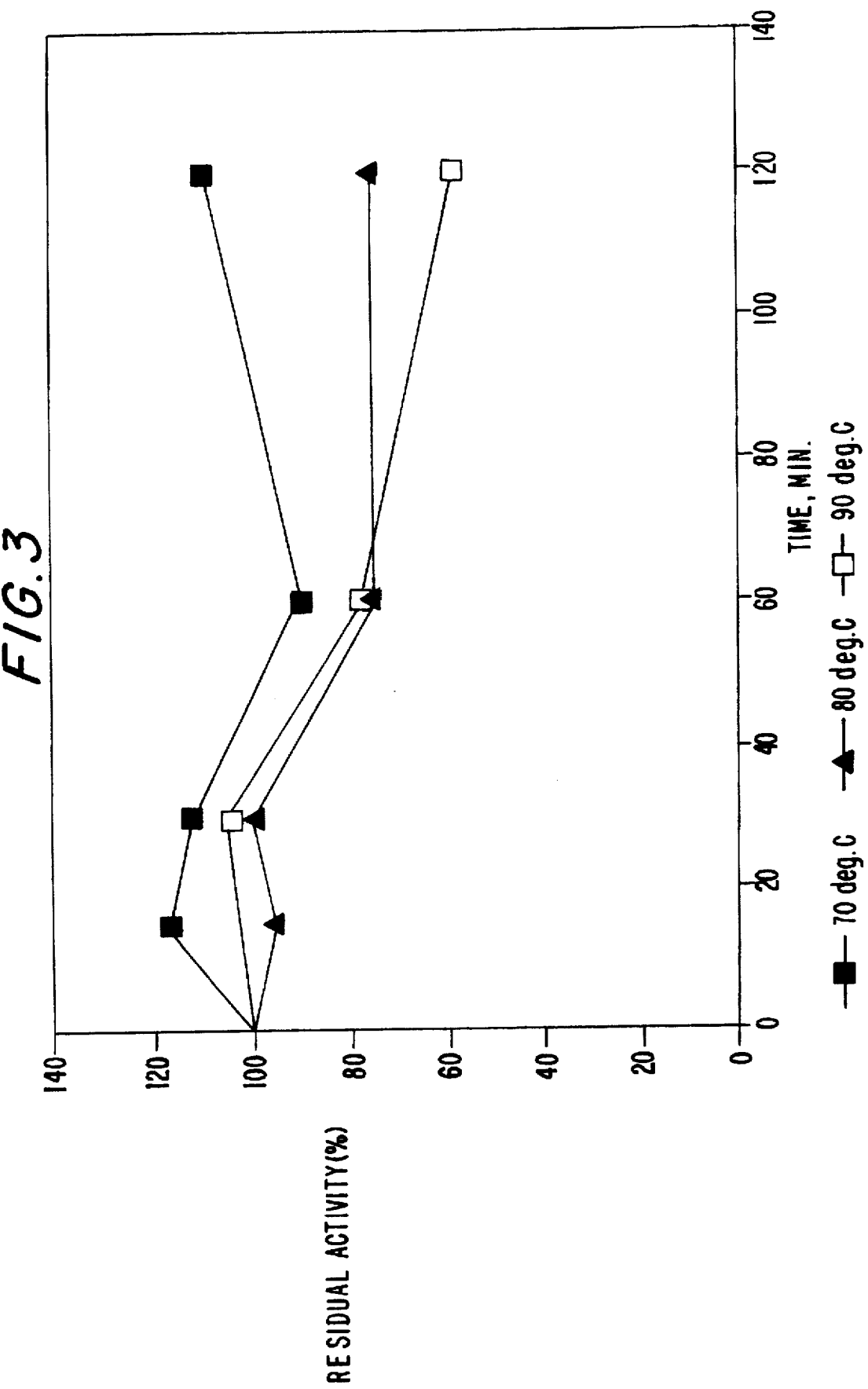
FIGS. 3 and 4 illustrate the thermostability of a crude and a purified peroxidase of the invention, respectively. For comparison.
Figure 4:
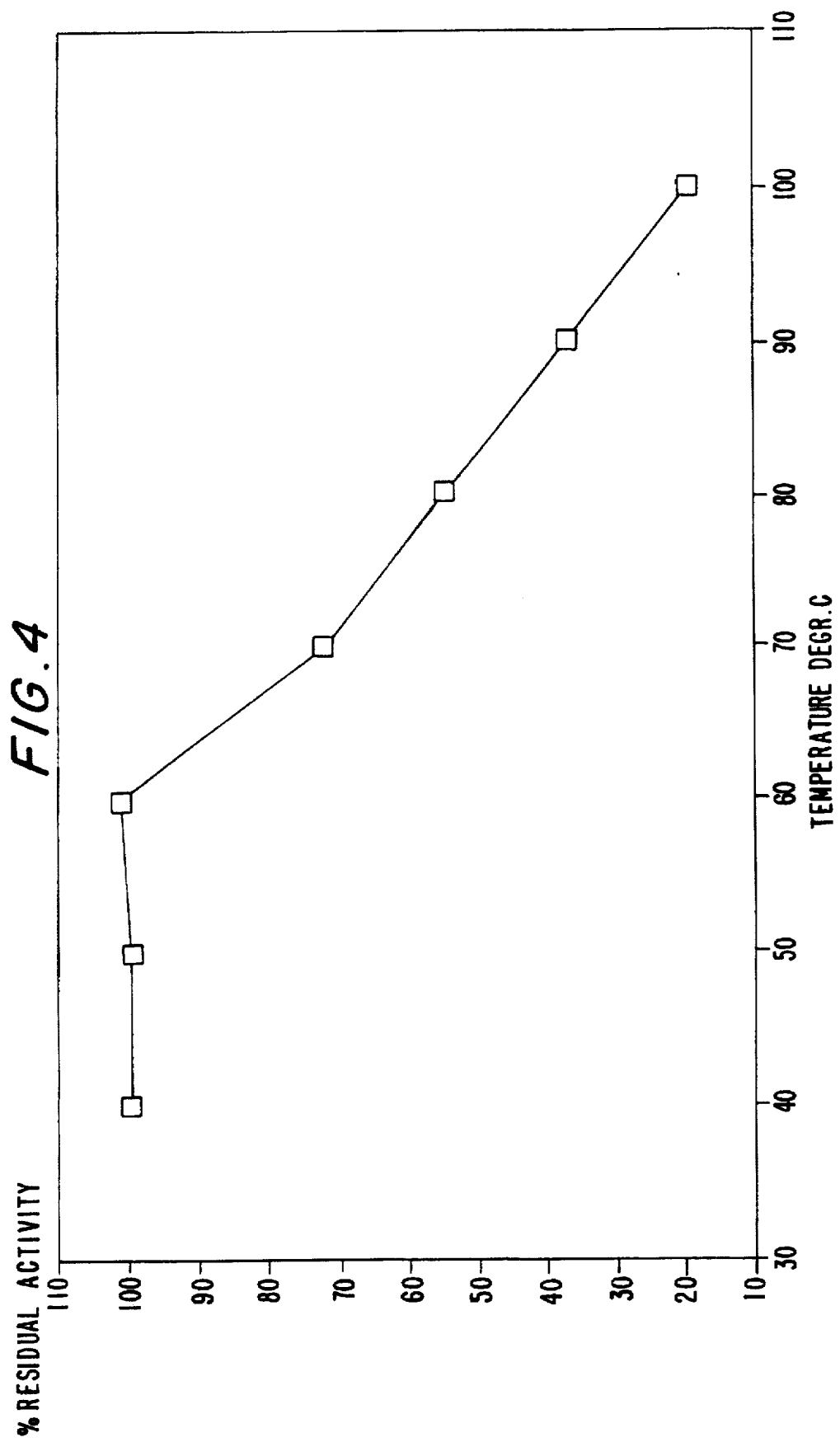
Figure 5:
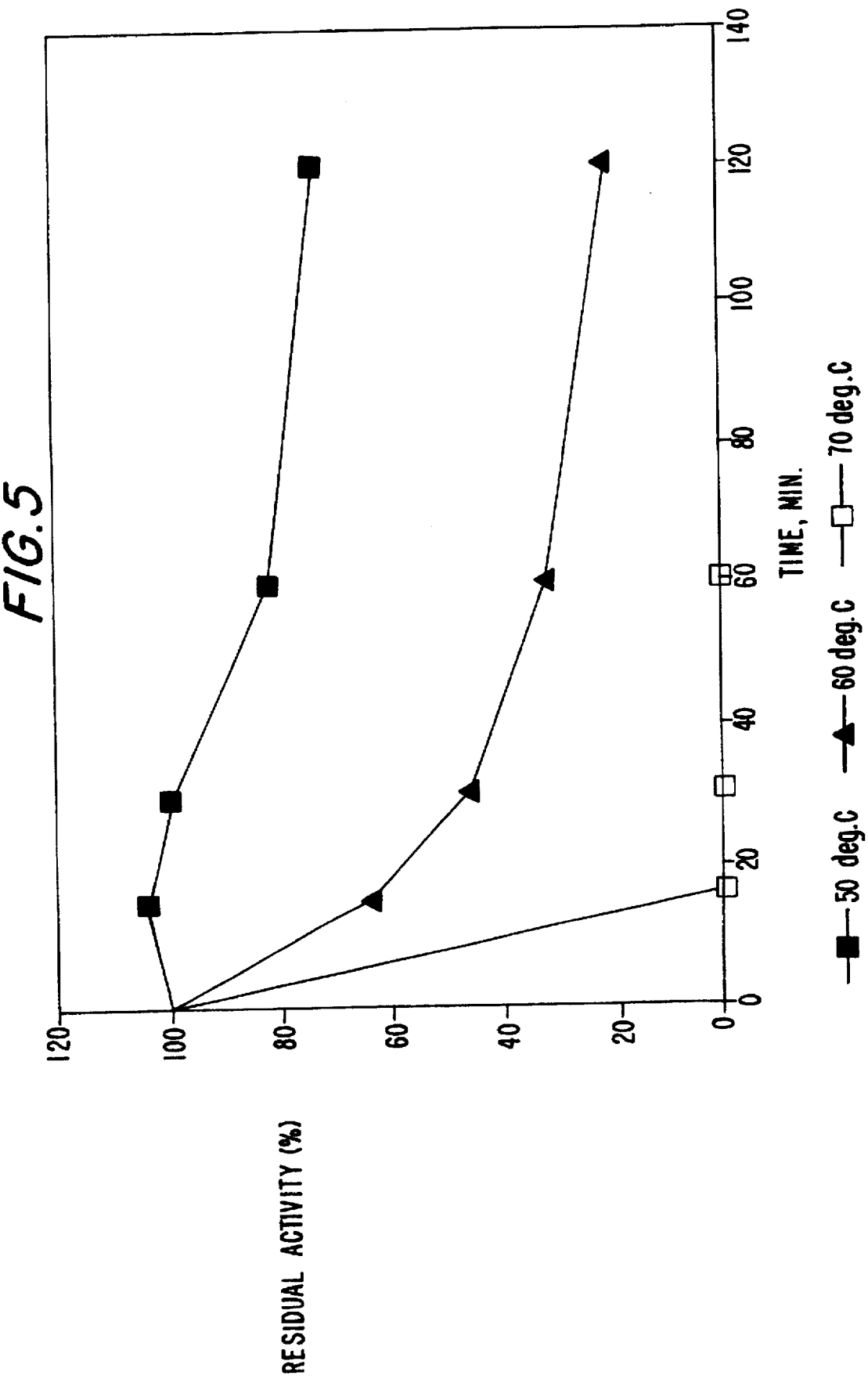
FIG. 5 shows the thermostability of a prior-art peroxidase preparation (from Coprinus). The measurements were made by incubating at the indicated time and temperature, then immediately diluting a sample 10 times in 0.1 M phosphate buffer pH 7 at 25° C., and measuring peroxidase activity (NOPA).
Figure 6:
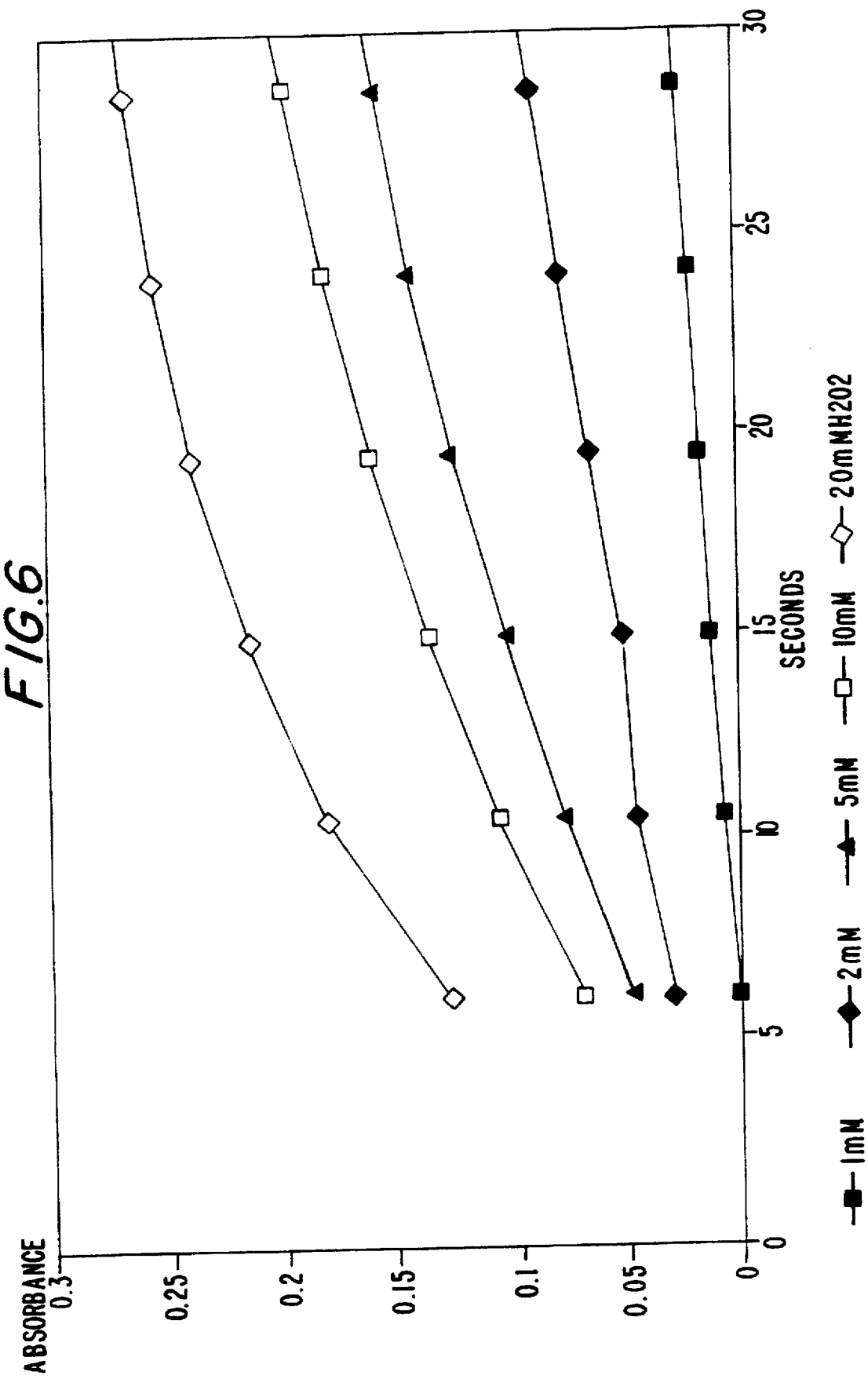
FIGS. 6 and 7 illustrate reaction at various $H_2O_2$ concentrations with peroxidase of the invention and prior-art peroxidase (Coprinus), respectively. Oxidation of ESBT+4-AA was followed by measuring the absorbance at 550 nm.
Figure 7:

Dyes were purchased from Aldrich Chemicals. Peroxycarboxylic acid references were synthesized according to W. E. Parker, C. Ricciuti, C. L. Ogg and D. Swern, *J. Am. Chem. Soc.*, 77, 4037 (1955). Spectra were recorded on a Hewlett Packard 8451 diode array spectrophotometer. The samples were scanned over the wavelength range 200 to 800 nm for one minute (spectra recorded every 6 sec). CMP is used below as an abbreviation for peroxidase derived form *Coprinus macrorhizus* (obtained from Chemical Dynamics). $H_2O_2$ is used synonymously with hydrogen peroxide. 2,4-DCP and PCA are used as abbreviations of 2,4-dichlorophenol and p-coumaric acid.

EXAMPLE 1

Bleaching of Congo Red in solution

To a solution of Congo Red (0.058 mM, 42 mg/l (dye content 93%, giving an initial abosrbance at 486 nm of 2.0) in phosphate buffer pH 7 (0.1 M) was added as bleaching agent either 2 mM $H_2O_2$, 1 mM peroxyoctanoic acid, or 2.5 mg/l CMP+0.25 mM $H_2O_2$. The experiments were performed at 25° C. in 1 cm quartz cells containing 1 ml. As listed below, only the peroxidase system gave any bleaching effect (monitored as observed change in absorbance at 486 nm in one minute).

| Bleaching system | Delta absorbance in 1 min |
|---|---|
| 2 mM $H_2O_2$ | 0.00 |
| 1 mM Peroxyoctanoic acid | 0.00 |
| 2.5 mg/l CMP + 0.25 mM $H_2O_2$ | 0.18 |

EXAMPLE 2

Bleach acceleration by phenolic compounds

Experiments were performed according to, example 1, except that the accelerating effect of adding various phenolic compounds as an additional substrate along with the peroxidase and $H_2O_2$ was examined. 2,4-DCP and PCA were added at a level of only 5 µM (0.82 mg/l in both cases).

| Bleaching system | Delta absorbance in 1 min |
|---|---|
| 2.5 mg/l CMP + 0.25 mM $H_2O_2$ | 0.18 |
| 2.5 mg/l CMP + 0.25 mM $H_2O_2$ + 5 µM 2,4-DCP | 0.74 |
| 2.5 mg/l CMP + 0.25 mM $H_2O_2$ + 5 µM PCA | 0.28 |

EXAMPLE 3

Bleaching of Acid Blue 45 in solution

Experiments were performed according to example 1 only using a solution of Acid Blue 45 (0.058 mM, 68 mg/l (dye content ca 40 %), giving an initial absorbance at 594 nm of 1.0). Bleaching was measured as change in absorbance at 594 nm.

| Bleaching system | Delta absorbance in 1 min |
|---|---|
| 2 mM $H_2O_2$ | 0.00 |
| 1 mM Peroxyoctanoic acid | 0.00 |
| 2.5 mg/l CMP + 0.25 mM $H_2O_2$ | 0.42 |

EXAMPLE 4

Bleach acceleration by phenolic compounds

Experiments were performed as described in example 2 except for using Acid Blue 45 as described in example 3.

| Bleaching system | Delta absorbance in 1 min |
|---|---|
| 2.5 mg/l CMP + 0.25 mM $H_2O_2$ | 0.42 |
| 2.5 mg/l CMP + 0.25 mM $H_2O_2$ + 5 µM 2,4-DCP | 0.69 |
| 2.5 mg/l CMP + 0.25 mM $H_2O_2$ + 5 µM PCA | 0.98 |

EXAMPLE 5

Solutions of Congo Red and Acid Blue 45 prepared, according to example 1 and 3, were treated with laccase (100 mg/l, crude enzyme preparation, derived from *Mycoliophtora thermophile*, available from Novo Nordisk as a special preparation, SP 315. Further information is available upon request). The difference in absorbance relative to a solution without enzyme added was measured after an incubation time of 16 hours.

| | Difference in absorbance after 16 hr. | |
|---|---|---|
| Bleaching agent | Congo Red (486 nm) | Acid Blue 45 (594 nm) |
| 0.1 g/l laccase | 0.29 | 0.09 |

EXAMPLE 6

Dye adsorption to textiles

In order to demonstrate that the effects seen in the above solution experiments are reflected on textiles present in such solutions, experiments were carried out in which clean cotton swatches were immersed in solutions of model textile dyes.

In one such experiment, the clean swatches were immersed in 0.058 mM and 0.012 mM solutions, respectively, of the dye Acid Blue 45 in 50 mM phosphate buffer (pH 7.0, 25° C.) and agitated for 60 min. The phosphate buffer was freshly prepared from water of a hardness equivalent to 1.6 mM $Ca^{2+}$. The swatch load was approx. 11 g cotton cloth/l.

Afterwards the swatches were rinsed in tap water and air-dried in the dark on a clean towel overnight. The remission at 600 nm (absorption region for blue substances) was measured on a Datacolor Elrephometer 2000.

The results of three treatments within the above prescriptions were as follows:

| | | Remission at 600 nm (%) | |
|---|---|---|---|
| | | Swatches retrieved from 0.058 mM Acid Blue 45 solution | Swatches retrieved from 0.012 mM Acid Blue 45 solution |
| 1. | Reference (buffer only) | 60 | 80 |
| 2. | 0.2 mM $H_2O_2$ | 58 | 79 |
| 3. | $H_2O_2$ as in 2 + 20 mg/l CMP | 74 | 90 |

Higher remission numbers here correspond to less blue color. Thus, the dye deposition on the clean swatches is considerably less in the solutions with peroxidase present.

EXAMPLE 7

Dye Adsorption to textiles

In another experiment, the procedure of example 6 was repeated in every detail, except that the dye in the solutions was Congo Red (at the same mM levels). Here, visual inspection of the resulting swatches unequivocally demonstrated the effect of the peroxidase: treatments 1 and 2 gave indistinguishably and heavily red-colored swatches, whereas only a faint yellowish color was seen on the swatches from treatment 3.

EXAMPLE 8

Dye adsorption to textiles

In this experiment, a particular type of test swatch was added for demonstrating dye adsorption effects. Each swatch consisted of 6 strips of textile, each 1.5 cm by 5 cm, sown together; the 6 textile brands were triacetate, bleached cotton, nylon, polyester, orlon, and viscose rayon.

The model washing liquor was a phosphate buffer prepared as in example 6 with 0.6 g/l linear alkylbenzenesulfonate added as a surfactant. Two 7 cm by 7 cm clean cotton swatches and one of the above multiswatches (also clean) were immersed in 1 litre of the washing liquor, with Congo Red added to a level of 0.012 mM, in each of two Terg-o-tometer beakers. In beaker 1, the bleaching system consisted of $H_2O_2$ at a level of 2 mM, in beaker 2, 20 mg of CMP was further added. A wash of 30 min at 40° C. with 60 rotations/min was performed, after which the swatches were rinsed in tap water and dried as above (example 6). This time, Hunter color difference readings were obtained for the multiswatches as follows:

|  | Hunter color difference readings | |
|---|---|---|
|  | Beaker 1 (only $H_2O_2$) | Beaker 2 ($H_2O_2$ + CMP) |
| Triacetate | 7.5 | 2.0 |
| Cotton | 69.9 | 35.0 |
| Nylon | 57.2 | 23.4 |
| Polyester | 16.0 | 5.0 |
| Orlon | 27.4 | 9.8 |
| Viscose | 69.7 | 30.7 |

(A value of 0 here indicates no change in color from the clean swatch and increasing numbers correspond to a visual impression of deeper color.)

Thus, the conclusion from example 6 is also valid here for all the textile brands studied.

EXAMPLE 9

Dye transfer from textile to textile

Swatches dyed with Congo Red as a model dye for azo textile dyes was prepared by immersing clean cotton swatches in a bath of Congo Red and sodium sulfate in demineralized water and keeping them there during a gradual heating to 90° C., ending with addition of further sodium sulfate and a period of a constant temperature of 90° C. After being dyed the swatches were rinsed in cold tap water and dried overnight between layers of gauze.

In the present experiment, washing was carried out in three Terg-o-tometer beakers under the same general conditions as in example 8. The contents of the beakers were:
Beaker 1: Only phosphate buffer with LAS (as in example 8)
Beaker 2: Buffer+LAS+2 mM $H_2O_2$
Beaker 3: As 2 with 20 mg/l CMP added In each beaker was introduced 2 Congo Red swatches, 7 cm by 7 cm, and one clean multiswatch (see example 8). After washing and drying as in example 8, the Hunter readings of the multiswatches were as follows:

|  | Beaker 1 | Beaker 2 | Beaker 3 |
|---|---|---|---|
| Triacetate | 3.4 | 3.4 | 2.8 |
| Cotton | 45.7 | 45.3 | 36.6 |
| Nylon | 41.6 | 40.9 | 35.6 |
| Polyester | 7.9 | 7.4 | 6.7 |
| Orlon | 14.7 | 15.0 | 11.2 |
| Viscose | 45.1 | 44.6 | 36.3 |

Thus, the swatches in beaker 1 suffer a substantial dye transfer which is not remedied by hydrogen peroxide alone, but reduced significantly by the peroxidase treatment.

The red swatches from the three beakers had essentially identical readings, showing that the peroxidase treatment does not change the dyeing any more than the other treatments.

EXAMPLE 10

Dye adsorption to textiles

For the purpose of studying the peroxidase effect in a more realistic washing environment, a powder detergent was composed as follows:

| Component | w/w % active material |
|---|---|
| Sodium carbonate | 22 |
| Sodium diphosphate | 17 |
| Sodium silicate | 7 |
| Sodium triphosphate | 5 |
| Sodium perborate monohydrate | 4 |
| Sodium nonanoyloxybenzenesulfonate | 5 |
| Sodium linear alkylbenzenesulfonate | 9 |
| Sodium alkyl sulfate | 4 |
| Various minor components: alcohol ethoxylate, diethylenetriamine pentaacetate, polyacrylate, polyethylene glycol, protease, optical brightener | each < 1 |
| Sodium sulfate and other miscellaneous | balance |

This detergent was used at a level of 2 g/l in water of a hardness equivalent to 1.6 mM $Ca^{2+}$ to produce a washing liquor in which pH was adjusted to 8.5. In this washing liquor, Congo Red was dissolved to a level of 0.012 mM. Beaker 1 was the reference (detergent+Congo Red); in beaker 2, CMP was added to a level of 20 mg/l. In both beakers, two clean cotton swatches and one clean multiswatch were added as in example 8. All other conditions were as in example 8 and the Hunter data for the multiswatches after the wash were as follows:

|  | Beaker 1 | Beaker 2 |
|---|---|---|
| Triacetate | 4.0 | 1.1 |
| Cotton | 62.5 | 2.3 |
| Nylon | 48.0 | 1.1 |
| Polyester | 4.0 | 0.4 |
| Orlon | 18.4 | 1.2 |
| Viscose | 66.3 | 1.3 |

Once again, the peroxidase clearly reduces—here almost eliminates—the amount of color deposited on the swatches.

EXAMPLE 11

Dye transfer from textile to textile

In this example, the detergent solution from example 9 was used in a Terg-o-tometer trial where two of the Congo Red-dyed swatches described above (example 9) were washed together with one clean multiswatch in each of two beakers. Beaker 1 contained just 1 litre of detergent solution, beaker 2 additionally contained 20 mg/l of CMP. The remaining conditions were as in example 8. The swatches, after retrieval from the washing liquor, rinsing and drying as above, showed the following Hunter color difference data:

|  | Beaker 1 | Beaker 2 |
|---|---|---|
| Triacetate | 2.3 | 1.1 |
| Cotton | 47.0 | 13.1 |
| Nylon | 36.0 | 11.3 |
| Polyester | 2.1 | 1.1 |
| Orlon | 6.5 | 2.7 |
| Viscose | 48.7 | 10.6 |

A considerable transfer of dye was thus observed in beaker 1, and this was significantly reduced by adding the peroxidase to the washing liquor.

Again, the dyed swatches were checked also, and no color difference was seen between the two treatments.

EXAMPLE 12

Bleaching of dyestuffs in solution
Peroxidase activity: In this example, the peroxidase activity is measured as follows. The following are mixed in a 30° C. thermostated 1 ml quartz cuvette:
200 μl 1 mM 4-aminoantipyrine (Sigma No. A-4382, 0.2 mg/ml)
200 μl N-ethyl-N-sulphobutyl-m-toluidin-Na (ESBT, 5.86 mg/ml)
200 μl 0.5 M phosphate buffer, pH 7.0
200 μl enzyme sample, diluted to 0.02–0.10 NOPA/ml 200 μl 10 mM hydrogen peroxide is added, and the absorbance at 550 nm is followed for 1 minute. The activity (in NOPA units) is calculated as the increase in absorbance within the first minute after addition of $H_2O_2$ multiplied by the dilution. The enzyme sample should be diluted so that the increase in absorbance per minute is within the limits 0.02 to 0.10.

Peroxidase production from *Bacillus pumilus*: Media were prepared as follows (ingredients in g/l):

|  | TY*3 |
| --- | --- |
| Trypticase, BBL g/l | 60 |
| Yeast Extract, Difco g/l | 15 |
| $FeSO_4 \cdot 7H_2O$ g/l | 0.025 |
| $MnSO_4 \cdot 4H_2O$ g/l | 0.0026 |
| $MgSO_4 \cdot 7H_2O$ g/l | 0.045 |
| pH | 7.3 |
|  | (Adjusted with KOH) |

The medium was autoclaved at 121° C. for 45 minutes.

|  | Agar3 |
| --- | --- |
| Pepton Bacto g/l | 6 |
| Pepticase g/l | 4 |
| Yeast Extract, Difco g/l | 3 |
| Meat Extract g/l | 1.5 |
| Glucose | 1 |
| pH | 7.3 |
| Agar (from Merck) | 20 |
|  | (added last) |

The agar was autoclaved at 121° C. for 45 minutes.
Inoculum agar: 10 Agar3 slants were inoculated with a freeze-dried peroxidase-producing strain of *B. pumilus* sign and incubated at 30° C. for 24 hours.
Inoculum media: Two 500 ml Shake flasks containing 100 ml TY*3 media were incoluated with one Agar3 slant and incubated at 30° C. and 250 rpm for 24 hours.
Peroxidase production: 50 Shake flasks containing 100 ml of TY*3 were incoluated each with 2 ml of inoculum described above. Then 2.5 ml of a sterile 40% (w/w) Glucose in water was added to each shake flask. The shake flasks were incubated at 30° C. for 48 hrs and then harvested. The final peroxidase activity was 1 NOPA/ml.

3250 ml culture broth were filtered through a Seitz Supra 100 filterplate and secondly through a Supra 50 plate to obtain a clear filtrate with an activity of 1.29 NOPA/ml.
Bleaching of dyes in solution: The above clear filtrate from *B. pumilus* (BPP) was tested. The dyestuffs tested were Direct Blue 1 (C.I. #24410, product of Keystone Aniline), Acid Red 151 (C.I. #26900, product of Sandoz), Procion Blue H ERD (product of ICI) and Procion Blue EXL (product of ICI).

A reaction solution was prepared, containing 50 mM sodium phosphate, 0.3 NOPA/ml of peroxidase, dyestuff (as indicated below) corresponding to an absorption maximum (in the visible range) of 0.025–0.035, and 0.25 mM at room temperature at the pH indicated below. After addition of $H_2O_2$ (added last), a spectral scan was made every minute for 12 minutes. Below, the change in absorbance at the wavelength of maximum absorption is listed.

| Dyestuff | pH | Absorbance change immediately/after 12 min | Wavelength |
| --- | --- | --- | --- |
| Acid Red 151 | 7.0 | 0.030/0.632 | 513 nm |
|  | 9.0 | 0.033/0.033 | 513 — |
|  | 10.5 | 0.027/0.030 | 513 — |
| Direct Blue 1 | 7.0 | 0.024/0.625 | 597 nm |
|  | 9.0 | 0.022/0.026 | 597 — |
|  | 10.5 | 0.009/0.023 | 597 — |
| Procion Blue H ERD | 7.0 | 0.022/0.021 | 617 nm |
|  | 9.0 | 0.009/0.022 | 617 — |
|  | 10.5 | 0.001/0.010 | 617 — |
| Procion Blue H EXL | 9.0 | 0.021/0.026 | 626 nm |
|  | 10.5 | 0.016/0.025 | 626 — |

When the two values of the absorbance change are close, the bleaching is practically instantaneous. Generally, bleaching over the entire visible range follows the above trends at the absorbance maximum.

In all cases, use of 0.25 mM $H_2O_2$ without enzyme left the dye unchanged.

EXAMPLE 13

Production of peroxidase from *Bacillus pumilus*
Media were prepared as follows (ingredients in g/l):

|  | TY*3 |
| --- | --- |
| Trypticase, BBL g/l | 60 |
| Yeast Extract, Difco g/l | 15 |
| $FeSO_4 \cdot 7H_2O$ g/l | 0.025 |
| $MnSO_4 \cdot 4H_2O$ g/l | 0.0026 |
| $MgSO_4 \cdot 7H_2O$ g/l | 0.045 |
| pH | 7.3 |
|  | (Adjusted with KOH) |

The medium was autoclaved at 121° C. for 45 minutes.

|  | Agar3 |
| --- | --- |
| Pepton Bacto g/l | 6 |
| Pepticase g/l | 4 |
| Yeast Extract, Difco g/l | 3 |
| Meat Extract g/l | 1.5 |
| Glucose | 1 |
| pH | 7.3 |
| Agar (from Merck) | 20 |
|  | (added last) |

The agar was autoclaved at 121° C. for 45 minutes.
Inoculum agar: 10 Agar3 slants were inoculated with 1 freeze dried *Bacillus pumilus* Strain no S197 and incubated at 30° C. for 24 hrs.
Inoculum media: Two 500 ml Shake flasks containing 100 ml TY*3 media were inoculated with one Agar3 slant and incubated at 30° C. and 250 rpm for 24 hrs.
Peroxidase production: 50 Shake flasks containing 100 ml of TY*3 were inoculated each with 2 ml of inoculum described above. Then 2.5 ml of a sterile 40% (w/w) glucose in water was added to each shake flask. The shake flasks were incubated at 30° C. for 48 hrs and then harvested. The final peroxidase activity was 1 NOPA/ml (NOPA measured at 20 mM $H_2O_2$).

EXAMPLE 14

Purification of peroxidase from *B. pumilus*

3250 ml of the culture broth obtained in Example 13 was filtered through a Seitz Supra 100 filter plate and secondly through a Supra 50 plate to obtain a clear filtrate with an activity of 1.29 NOPA/ml.

To 900 ml of the filtrate was added 70 g Amberlite XAD16 hydrophobic resin and the mixture was stirred overnight at 4° C. The resin was isolated by decantation and washed with 10% v/v ethanol. Peroxidase was extracted from the resin with 200 ml 50% v/v ethanol which was evaporated to 72 ml with an activity of 13.8 NOPA/ml (yield: 86%).

Figure 8:
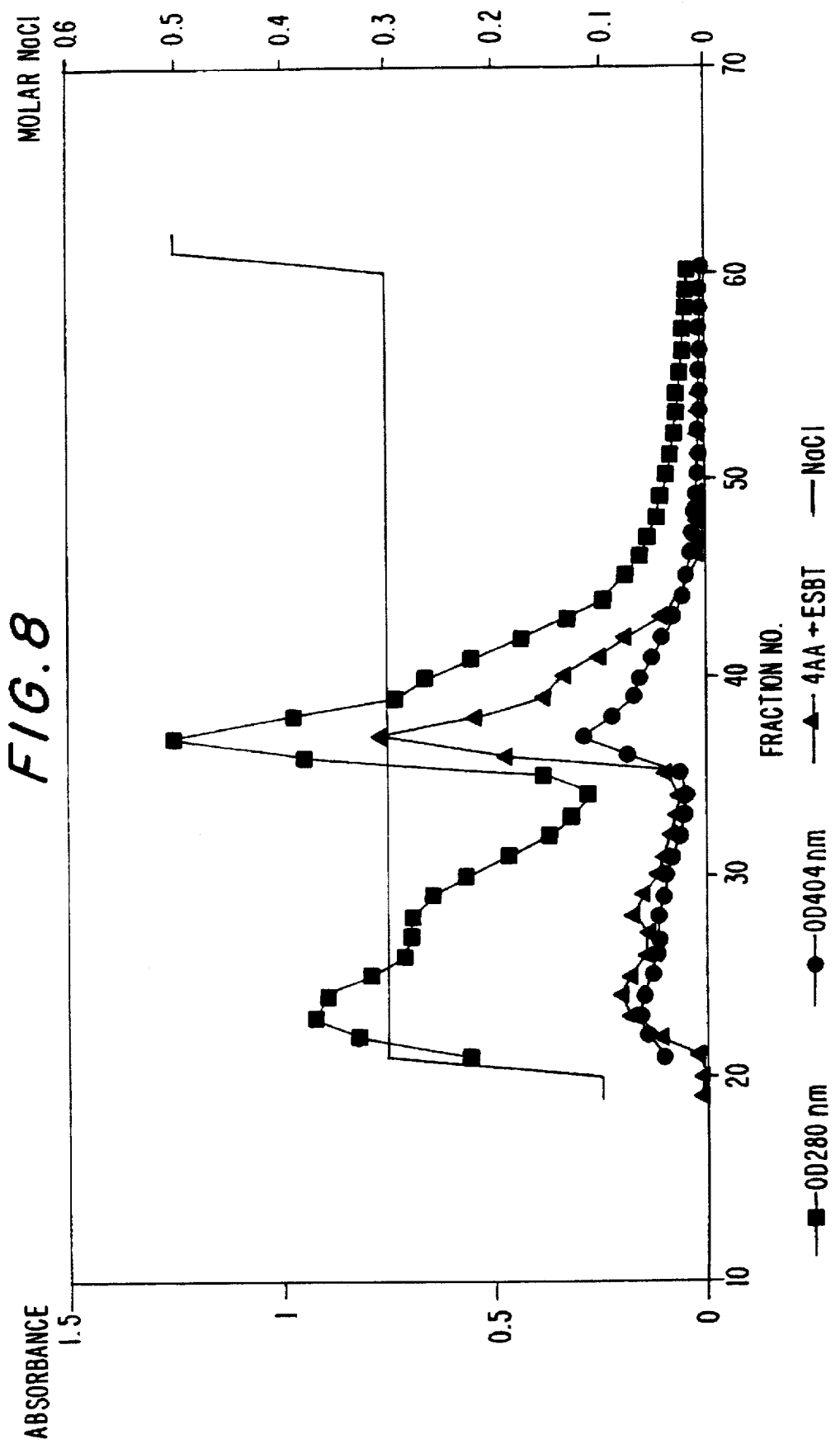
FIGS. 8–11 show chromatograms from purification of peroxidase of the invention. Details are given in Example 14.

The evaporated peroxidase extract was applied to a DEAE Sepharose FF column (5×8 cm) equilibrated with 20 mM phosphate pH 7. The column was washed with more than one volume of buffer containing 0.1 M NaCl and peroxidase was eluted with buffer containing 0.3 M NaCl. Fractions of 10 ml were collected and pooled in three pools according to protein (A280) and activity profiles (FIG. 8):

|   | Fraction no. | ml | A280 | A404 | NOPA/ml | Yield |
|---|---|---|---|---|---|---|
| Pool A | 23–26 | 40 | 8.14 | 1.37 | 2.33 | 9.3% |
| Pool B | 27–30 | 40 | 6.41 | 1.05 | 2.17 | 8.7% |
| Pool C | 36–42 | 40 | 8.90 | 1.84 | 6.89 | 27.7% |
| Total yield: 45.7% | | | | | | |

A 90 ml sample with 7.34 NOPA/ml of pool C was added 1.6 M ammonium sulphate to a conductivity of 108 mS (pH 7.05) and applied on an Octyl-Sepharose column (5×11) cm) equilibrated with 0.8 M ammonium sulphate pH 7. Unbound material was eluted with 0.8 M ammonium sulphate and peroxidase activity was then eluted with a linear gradient of ammonium sulphate from 0.8 to 0 molar (pure water).

Figure 9:
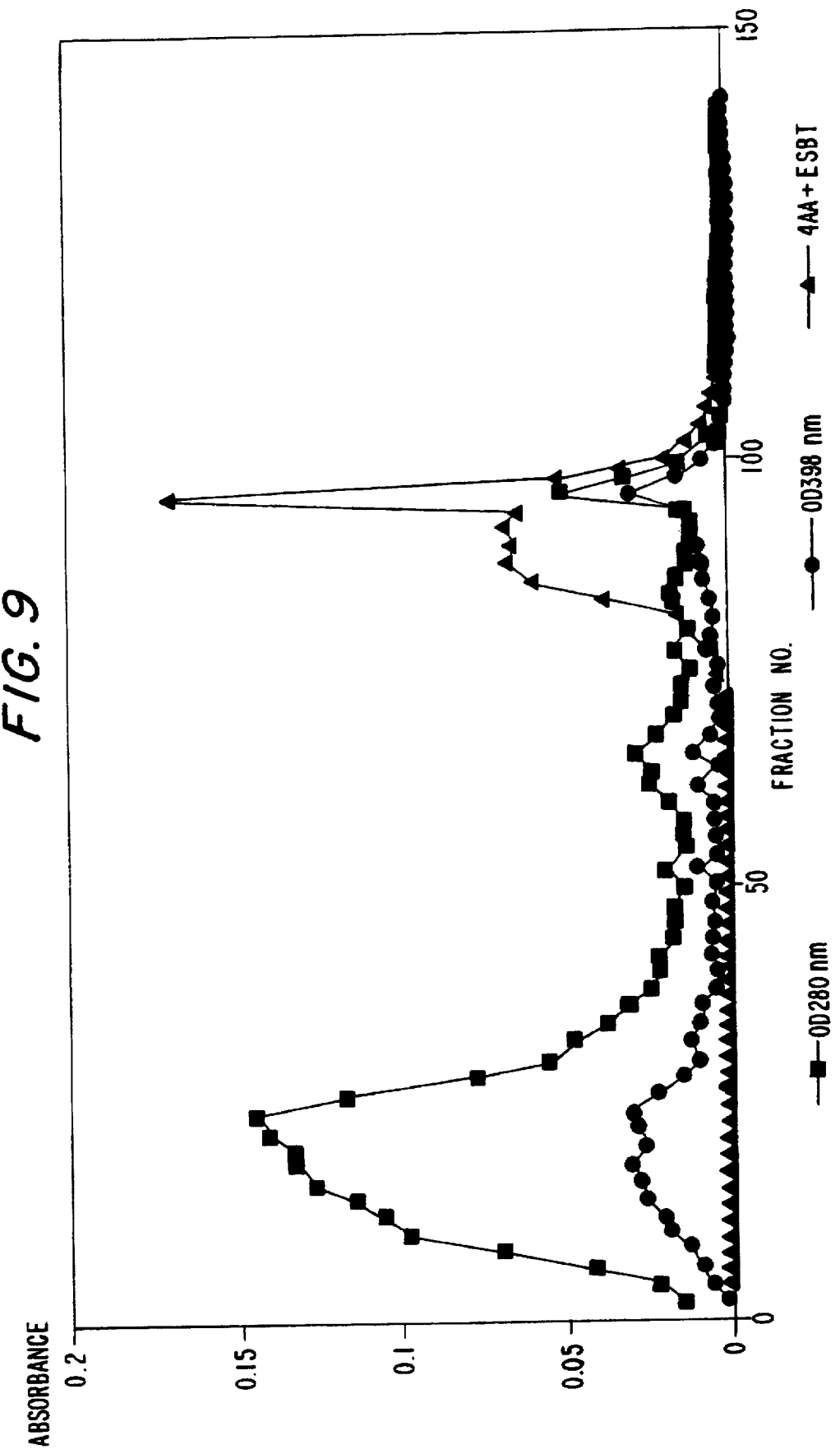

Fractions of 10 ml were collected and pooled in three pools according to the peroxidase activity (FIG. 9):

|   | Fraction no. | ml | A280 | A398 | NOPA/ml | Yield |
|---|---|---|---|---|---|---|
| Pool I | 84–92 | 90 | 0.26 | 0.19 | 1.47 | 20.0% |
| Pool II | 94–96 | 30 | 0.58 | 0.37 | 2.09 | 9.5% |
| Pool III | 97–100 | 40 | 0.55 | 0.30 | 1.57 | 9.5% |
| Total yield: 39% | | | | | | |

Figure 10:
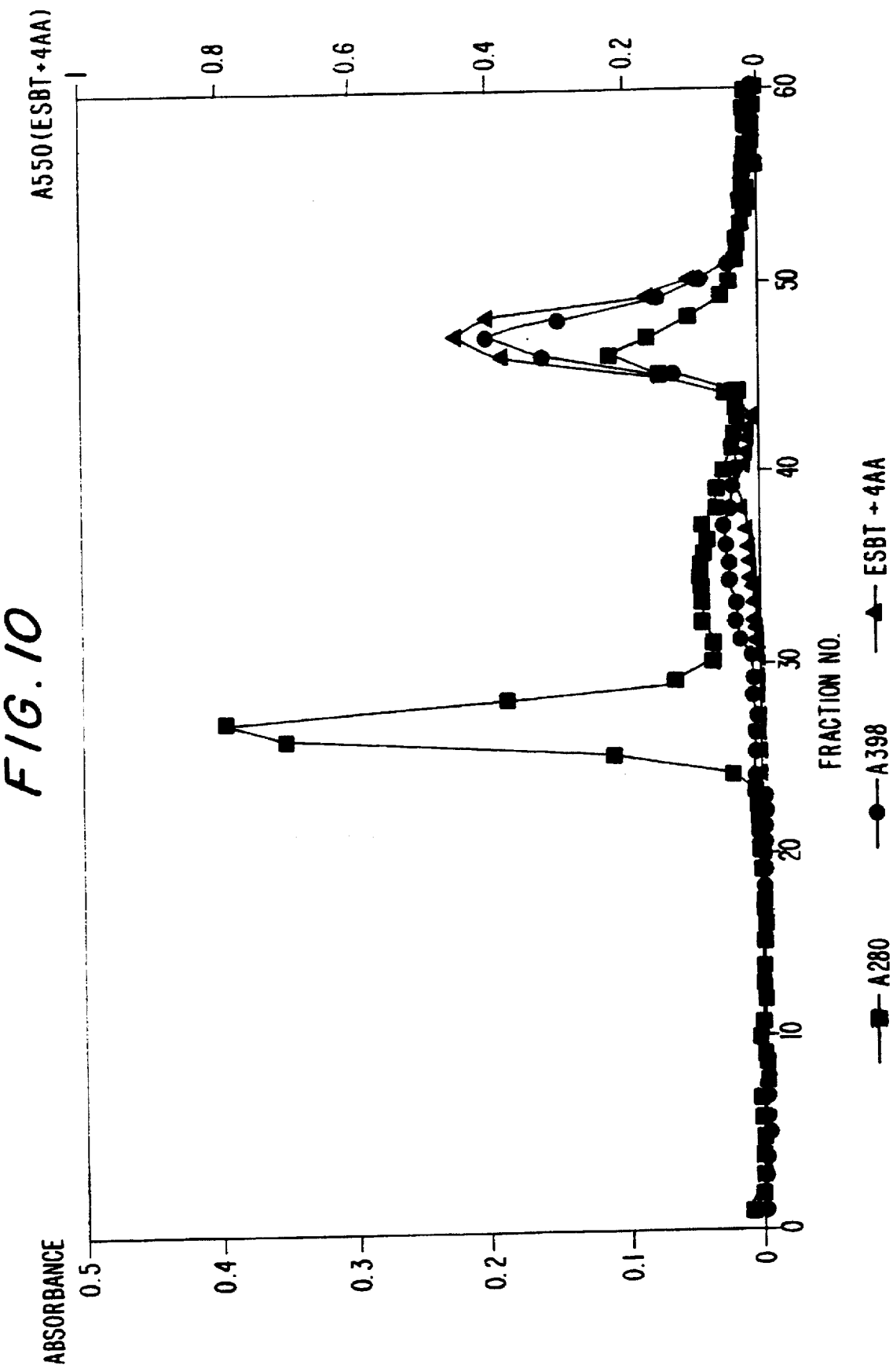

A sample of Pool III was concentrated by ultrafiltration on a 50 ml Amicon stirred cell with a DDS GS90PP membrane. A 7.5 ml concentrated sample with an activity of 131.2 NOPA/ml was applied to a Sephacryl-S200 column (2.5×85 cm) equilibrated with 12.5 mM phosphate buffer pH 7.0 and eluted with the same buffer at a flow rate of 0.9 ml/min. Fractions of 9.8 ml were collected and pooled according to peroxidase activity and spectral properties (Rz-value: A398/A280) (FIG. 10):

|   | Fraction no. | ml | A280 | A398 | NOPA/ml | Yield |
|---|---|---|---|---|---|---|
| Pool A | 47–50 | 38 | 0.47 | 1.22 | 11.2 | 43.3% |
| Pool B | 45 | 9.8 | 0.73 | 0.69 | 6.76 | 6.7% |
| Pool C | 46 | 9.8 | 1.16 | 1.65 | 15.97 | 15.8% |
| Total yield: 65.8% | | | | | | |

The mass spectrum of Pool IA show one major peak at Mw 2214.0/2228.1 and two minor peaks at Mw 972.8 and 1768.1, respectively. The amino acid sequence of the major component was shown to be SEQ ID NO:4 where each Xaa is believed to be cysteine through which a heme group (responsible for the A398 absorbance) can be bound, i.e., the amino acid sequence SEQ ID NO:1.

Figure 11:
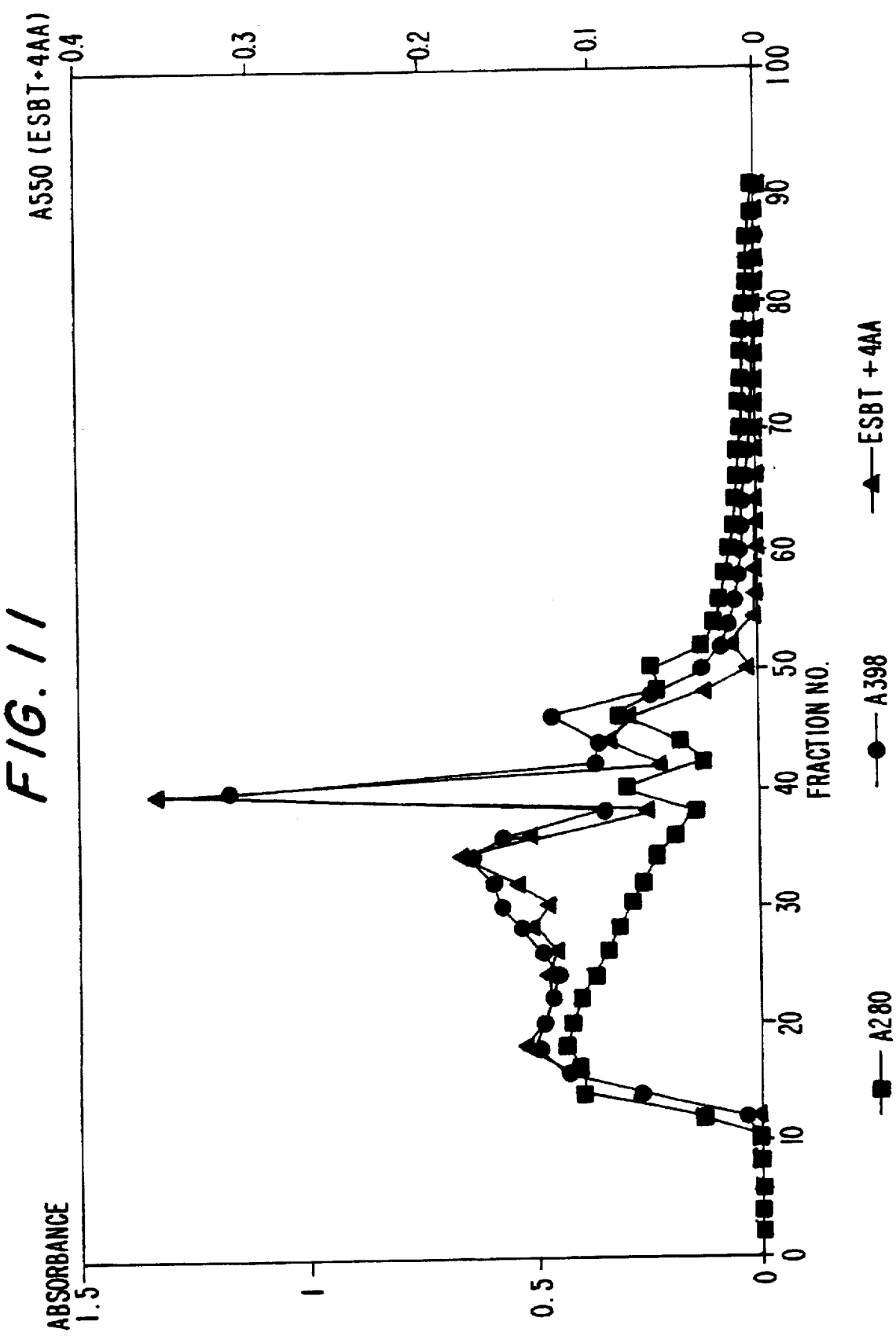

A sample of pool II was concentrated by ultrafiltration on a 50 ml Amicon stirred cell with a DDS GS90PP membrane. A 10 ml concentrated sample with an activity of 143.8 NOPA/ml was applied to a AcA 202 column (2.5×85 cm) equilibrated with 12.5 mM phosphate buffer pH 7.0 and eluted with the same buffer at a flow rate of 0.4 ml/min. Fractions of 5 ml were collected and monitored for A280, A398 and peroxidase activity (FIG. 11).

This AcA 202 gel is claimed by the manufacturer to separate molecules in the range from 1 kD to 15 kD. From the chromatogram it is seen that a wide range of relatively low Mw substance was eluted and all showing the same peroxidase activity relative to the A398 (Soret) absorbance.

EXAMPLE 15

Bleaching of kraft pulp

The peroxidase used in this example was the permeate from ultrafiltration of the supernatant from alcohol precipitation of a cell-free culture broth (obtained essentially as in Example 13).

1 g hardwood (birch) kraft pulp, delignified by oxygen, was blended in 250 ml water adjusted to pH 8.0–8.2 with NaOH. $H_2O_2$ was added to a concentration of 1% (0.3 M), and the above peroxidase preparation was added to a dosage of 0.32 NOPA/ml. The mixture was incubated at 40° C. for 2 hours. Then the pulp was collected on a Buchner funnel and washed with sufficient water to obtain a clear filtrate. The pulp was pressed and dried, and the ISO brightness of the obtained sheet was measured. A reference was made in the same way without the enzyme.

Invention: 57.2% ISO brightness

Reference: 55.6% ISO brightness

EXAMPLE 16

Bleaching of CTMP pulp

The experiment of Example 15 was repeated at 30° C. with CTMP softwood (pine) pulp.

Invention: 59.7% ISO brightness

Reference: 56.1% ISO brightness

EXAMPLE 17

Bleaching of dyes in solution

The effect of the peroxidase preparation of the invention in bleaching a dissolved textile dye was tested. The dyestuffs tested were Direct Blue 1 (C.I. #24410, product of Keystone Aniline), Acid Red 151 (C.I. #26900, product of Sandoz), Procion Blue HERD (product of ICI) and Procion Blue H EXL (product of ICI). The peroxidase preparation was cell-free culture broth prepared essentially as in Example 13.

A reaction solution was prepared, containing 50 mM sodium phosphate, 0.3 NOPA/ml of peroxidase, dyestuff (as indicated below) corresponding to an absorption maximum (in the visible range) of 0.025–0.035, and 0.25 mM $H_2O_2$ at room temperature at the pH indicated below. After addition of $H_2O_2$ (added last), a spectral scan was made every minute for 12 minutes. Below, the change in absorbance at the wavelength of maximum absorption is listed.

| Dyestuff | pH | Absorbance change immediately/after 12 min | Wavelength |
|---|---|---|---|
| Acid Red 151 | 7.0 | 0.030/0.032 | 513 nm |
| | 9.0 | 0.033/0.033 | 513 — |
| | 10.5 | 0.027/0.030 | 513 — |
| Direct Blue 1 | 7.0 | 0.024/0.025 | 597 nm |
| | 9.0 | 0.022/0.026 | 597 — |
| | 10.5 | 0.009/0.023 | 597 — |
| Procion Blue H ERD | 7.0 | 0.022/0.021 | 617 nm |
| | 9.0 | 0.009/0.022 | 617 — |
| | 10.5 | 0.001/0.010 | 617 — |
| Procion Blue H EXL | 9.0 | 0.021/0.026 | 626 nm |
| | 10.5 | 0.016/0.025 | 626 — |

When the two values of the absorbance change are close, the bleaching is practically instantaneous. Generally, bleaching over the entire visible range follows the above trends at the absorbance maximum.

In all cases, use of 0.25 mM $H_2O_2$ without enzyme left the dye unchanged.

This example illustrates the potential usefulness of the peroxidase preparation of the invention in preventing surplus dye from strongly-coloured fabric from being redeposited during washing.

---

We claim:

1. A process for bleaching a textile dye in a solution or dispersion, the process comprising incorporating an effective amount of an enzyme exhibiting oxidase activity on phenolic compounds into the solution or dispersion.

* * * * *

UNITED STATES PATENT AND TRADEMARK OFFICE
CERTIFICATE OF CORRECTION

PATENT NO.    : 5,712,153

DATED         : January 27, 1998

INVENTOR(S)   : Damhus et al.

It is certified that error appears in the above-identified patent and that said Letters Patent is hereby corrected as shown below:

Front Page, left column, after "[73] Assignee: Novo Nordisk A/S. Bagsvaerd, Denmark" insert --; The Proctor & Gamble Company, Cincinatti, Ohio--

Signed and Sealed this

Eleventh Day of April, 2000

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5..8
        ( D ) OTHER INFORMATION: /note="Heme group attached to Cys in positions 5 and 8"

( x i ) SEQUENCE DESCRIPTION: SEQ ID NO:1:

Gln Glu Gln Thr Cys Ile Ser Cys His Gly Asp Asn Met Gln
    1                 5                                10

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5..8
        ( D ) OTHER INFORMATION: /note="Heme group attached to Cys in positions 5 and 8"

( x i ) SEQUENCE DESCRIPTION: SEQ ID NO:2:

Phe Val Gln Lys Cys Ala Gln Cys His Thr Val Glu Lys Gly
    1                 5                                10

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site (B) LOCATION: 1..4
          (D) OTHER INFORMATION: /note="Heme group attached to Cys
                in positions 1 and 4"

(ix) FEATURE:
          (A) NAME/KEY: Modified-site
          (B) LOCATION: 1
          (D) OTHER INFORMATION: /note="R attached to Cys in
                position 1, wherein R is a peptide chain of 0-10 amino
                acids"

(ix) FEATURE:
          (A) NAME/KEY: Modified-site
          (B) LOCATION: 5
          (D) OTHER INFORMATION: /note="R' attached to His in
                position 5, wherein R' is a peptide chain of 0-10 amino
                acids"

(xi) SEQUENCE DESCRIPTION: SEQ ID NO:3:

Cys  Ile  Ser  Cys  His
1                    5

(2) INFORMATION FOR SEQ ID NO:4:

(i) SEQUENCE CHARACTERISTICS:
          (A) LENGTH: 14 amino acids
          (B) TYPE: amino acid
          (C) STRANDEDNESS: single
          (D) TOPOLOGY: linear (ix) FEATURE:
          (A) NAME/KEY: Modified-site
          (B) LOCATION: 5..8
          (D) OTHER INFORMATION: /note="Xaa in positions 5 and 8
                represents any amino acid"

(xi) SEQUENCE DESCRIPTION: SEQ ID NO:4:

Gln  Glu  Gln  Thr  Xaa  Ile  Ser  Xaa  His  Gly  Asp  Asn  Met  Gln
1                    5                        10

(2) INFORMATION FOR SEQ ID NO:5:

(i) SEQUENCE CHARACTERISTICS:
          (A) LENGTH: 9 amino acids
          (B) TYPE: amino acid
          (C) STRANDEDNESS: single
          (D) TOPOLOGY: linear (ix) FEATURE:
          (A) NAME/KEY: Modified-site
          (B) LOCATION: 5..8
          (D) OTHER INFORMATION: /note="Heme group attached to Cys
                in positions 5 and 8"

(ix) FEATURE:
          (A) NAME/KEY: Modified-site
          (B) LOCATION: 9
          (D) OTHER INFORMATION: /note="R' attached to His in
                position 9, wherein R' is a peptide chain of 0-10 amino
                acids"

(xi) SEQUENCE DESCRIPTION: SEQ ID NO:5:

Gln  Glu  Gln  Thr  Cys  Ile  Ser  Cys  His
1                    5

(2) INFORMATION FOR SEQ ID NO:6:

(i) SEQUENCE CHARACTERISTICS:
          (A) LENGTH: 10 amino acids
          (B) TYPE: amino acid
          (C) STRANDEDNESS: single
          (D) TOPOLOGY: linear (ix) FEATURE:

(A) NAME/KEY: Modified-site
            (B) LOCATION: 1..4
            (D) OTHER INFORMATION: /note="Heme group attached to Cys
                in positions 1 and 4"

(ix) FEATURE:
            (A) NAME/KEY: Modified-site
            (B) LOCATION: 1
            (D) OTHER INFORMATION: /note="R attached to Cys in
                position 1, wherein R is a peptide chain of 0-10 amino
                acids"

(xi) SEQUENCE DESCRIPTION: SEQ ID NO:6:

Cys  Ile  Ser  Cys  His  Gly  Asp  Asn  Met  Gln
    1                   5                        10